(12) United States Patent
Verma et al.

(10) Patent No.: US 11,484,278 B2
(45) Date of Patent: *Nov. 1, 2022

(54) ASSESSMENT OF LABELED PROBES IN A SUBJECT

(71) Applicant: Biogen MA Inc., Cambridge, MA (US)

(72) Inventors: Ajay Verma, Needham, MA (US); Jack Hoppin, Boston, MA (US); Jacob Hesterman, Brighton, MA (US)

(73) Assignee: Biogen MA Inc., Cambridge, MA (US)

( * ) Notice: Subject to any disclaimer, the term of this patent is extended or adjusted under 35 U.S.C. 154(b) by 1397 days.

This patent is subject to a terminal disclaimer.

(21) Appl. No.: 14/774,577

(22) PCT Filed: Mar. 12, 2014

(86) PCT No.: PCT/US2014/024928
§ 371 (c)(1),
(2) Date: Sep. 10, 2015

(87) PCT Pub. No.: WO2014/151078
PCT Pub. Date: Sep. 25, 2014

(65) Prior Publication Data
US 2016/0029983 A1 Feb. 4, 2016

Related U.S. Application Data

(60) Provisional application No. 61/798,709, filed on Mar. 15, 2013.

(51) Int. Cl.
*A61B 6/00* (2006.01)
*A61B 6/03* (2006.01)
(Continued)

(52) U.S. Cl.
CPC .......... *A61B 6/4405* (2013.01); *A61B 5/0022* (2013.01); *A61B 5/0071* (2013.01);
(Continued)

(58) Field of Classification Search
CPC ..... A61B 6/4405; A61B 6/037; A61B 6/4258; A61B 6/481; A61B 6/501; A61B 5/501;
(Continued)

(56) References Cited

U.S. PATENT DOCUMENTS 4,633,881 A 6/1987 Moore et al.
4,682,604 A 7/1987 Fymat et al.
(Continued)

FOREIGN PATENT DOCUMENTS

AU 2014/210083 A1 8/2015
DE 26 41 039 A1 3/1978
(Continued)

OTHER PUBLICATIONS

Schulz et al. "Simultaneous assessment of rodent behavior and neurochemistry using a miniature positron emission tomograph." Nature Methods vol. 8, No. 4. Apr. 2011, pp. 347-354. (Year: 2011).*

(Continued)

*Primary Examiner* — Angela M Hoffa
(74) *Attorney, Agent, or Firm* — Wolf, Greenfield & Sacks, P.C.

(57) ABSTRACT

Wearable apparatus and method of using same for tracking a labeled probe in a subject are disclosed.

20 Claims, 3 Drawing Sheets

(51) Int. Cl.

| | |
|---|---|
| *A61B 5/00* | (2006.01) |
| *A61B 5/0275* | (2006.01) |
| *G16H 40/67* | (2018.01) |
| *G01T 1/164* | (2006.01) |
| *G01T 1/29* | (2006.01) |

(52) U.S. Cl.
CPC ........ *A61B 5/02755* (2013.01); *A61B 5/6803* (2013.01); *A61B 6/4216* (2013.01); *A61B 6/4258* (2013.01); *A61B 6/481* (2013.01); *A61B 6/501* (2013.01); *A61B 6/563* (2013.01); *G01T 1/1641* (2013.01); *G01T 1/2928* (2013.01); *G01T 1/2985* (2013.01); *G16H 40/67* (2018.01); *A61B 5/4088* (2013.01); *A61B 6/037* (2013.01)

(58) Field of Classification Search
CPC .... A61B 5/0071–0075; A61B 5/02755; A61B 5/6803; A61B 5/6814; G01T 1/16–1666; G01T 1/2921–2957; G01T 1/2985
See application file for complete search history.

(56) References Cited

U.S. PATENT DOCUMENTS

| | | | |
|---|---|---|---|
| 5,007,427 A | 4/1991 | Suzuki et al. | |
| 5,111,818 A | 5/1992 | Suzuki et al. | |
| 5,583,343 A | 12/1996 | Dilmanian et al. | |
| 5,647,363 A | 7/1997 | Rabito et al. | |
| D400,196 S | 10/1998 | Cameron et al. | |
| 5,967,983 A | 10/1999 | Ashburn | |
| 6,242,743 B1 | 6/2001 | DeVito et al. | |
| 6,429,431 B1 | 8/2002 | Wilk | |
| 6,574,513 B1 | 6/2003 | Collura et al. | |
| 6,583,420 B1* | 6/2003 | Nelson | A61B 6/4233 250/363.05 |
| 6,690,397 B1 | 2/2004 | Daignault, Jr. | |
| 6,693,291 B2* | 2/2004 | Nelson | A61B 6/4233 250/363.01 |
| 7,015,460 B2* | 3/2006 | Nelson | A61B 6/4233 250/252.1 |
| D533,875 S | 12/2006 | Miles et al. | |
| 7,147,372 B2* | 12/2006 | Nelson | A61B 6/4233 378/207 |
| 7,391,028 B1 | 6/2008 | Rubenstein | |
| 7,500,746 B1* | 3/2009 | Howell | G02C 11/10 351/158 |
| 7,541,599 B2* | 6/2009 | Moritake | A61B 5/6805 250/472.1 |
| D614,634 S | 4/2010 | Nilsen | |
| 7,737,410 B2 | 6/2010 | Rubenstein | |
| D619,609 S | 7/2010 | Meziere | |
| 7,884,331 B2 | 2/2011 | Majewski et al. | |
| 8,158,950 B2 | 4/2012 | Rubenstein | |
| 8,324,589 B2 | 12/2012 | Rubenstein | |
| D690,716 S | 10/2013 | Thomsen et al. | |
| 8,822,924 B2* | 9/2014 | Valentino | G01J 1/0488 250/336.1 |
| 9,044,150 B2 | 6/2015 | Brumback et al. | |
| 9,110,115 B2 | 8/2015 | Marashdeh et al. | |
| 9,226,717 B2 | 1/2016 | Tashima et al. | |
| 9,429,661 B2* | 8/2016 | Valentino | G01J 1/0488 |
| 9,655,573 B2* | 5/2017 | Majewski | A61B 6/4405 |
| D795,890 S | 8/2017 | Verma et al. | |
| 9,924,913 B2* | 3/2018 | Majewski | A61B 6/4405 |
| 9,943,278 B2 | 4/2018 | Nagler et al. | |
| 10,206,639 B2* | 2/2019 | Verma | A61B 6/4405 |
| 11,147,524 B2* | 10/2021 | Verma | A61B 6/037 |
| 2004/0259270 A1 | 12/2004 | Wolf | |
| 2007/0018107 A1* | 1/2007 | Fukuda | G01T 1/2023 250/361 R |
| 2008/0149835 A1* | 6/2008 | Moritake | A61N 5/1048 250/336.1 |
| 2009/0299210 A1 | 12/2009 | Marcarian | |
| 2010/0100848 A1 | 4/2010 | Ananian et al. | |
| 2011/0054577 A1 | 3/2011 | Latham | |
| 2013/0071826 A1 | 3/2013 | Johnson | |
| 2014/0012108 A1 | 1/2014 | McPeak | |
| 2014/0312242 A1* | 10/2014 | Valentino | G01P 13/00 250/395 |
| 2014/0321723 A1 | 10/2014 | Orcutt et al. | |
| 2014/0378794 A1 | 12/2014 | Conrad et al. | |
| 2015/0182121 A1 | 7/2015 | Barbour et al. | |
| 2015/0213214 A1 | 7/2015 | Patak et al. | |
| 2015/0268355 A1* | 9/2015 | Valentino | G01T 1/167 455/456.1 |
| 2015/0346353 A1 | 12/2015 | Gray | |
| 2016/0008204 A1 | 1/2016 | Elliot | |
| 2016/0058644 A1 | 3/2016 | Cheathan, III et al. | |
| 2017/0086763 A1* | 3/2017 | Verma | A61B 6/4405 |
| 2019/0200943 A1* | 7/2019 | Verma | A61B 6/4258 |
| 2019/0320989 A1* | 10/2019 | Verma | G01T 1/16 |

FOREIGN PATENT DOCUMENTS

| | | |
|---|---|---|
| DE | 196 07 157 A1 | 2/1997 |
| DE | 10261342 A1 | 7/2004 |
| WO | WO 2010/033159 A1 | 3/2010 |
| WO | WO 2010/038176 A1 | 4/2010 |
| WO | WO 2014/114555 A1 | 7/2014 |

OTHER PUBLICATIONS

Bauer et a;. "Concept of an upright weable positron emission tomography imager in humans." Brain and Behavior, 6: e00530. 2016. 10 pages. (Year: 2016).*

Ishaque, Imaging the Brain in Real-Time with a PET-Enabled "Helmet-Cam". http://www.geglobalresearch.com/blog/imaging-brain-real-time-pet-enabled-helmet-cam [dated Sep. 30, 2014; last accessed Dec. 15, 2016] 5 pages.

International Search Report and Written Opinion for International application No. PCT/US2014/024928 dated Jul. 17, 2014.

International Preliminary Report on Patentability for for International application No. PCT/US2014/024928 dated Sep. 24, 2015.

Prout et al., Detector concept for OPET, a combined PET and optical imaging system. IEEE. 2003;4:2252-6.

Bojsen et al., Portable cadmium telluride detectors and their applicability for external measurement of 51Cr-EDTA clearance. Int J Appl Radiat Isot. Oct. 1981;32(10):719-27.

* cited by examiner

ASSESSMENT OF LABELED PROBES IN A SUBJECT

CROSS REFERENCE TO RELATED APPLICATIONS

This application is a national stage filing under 35 U.S.C. ◊ 371 of International Patent Application Serial No. PCT/US2014/024928, filed Mar. 12, 2014, which claims the benefit of priority under 35 U.S.C. ◊ 119(e) of U.S. Provisional Application Ser. No. 61/798,709, filed Mar. 15, 2013, the disclosures of each of which are incorporated herein by reference in their entirety.

BACKGROUND

1. Field of the Invention

The present invention generally relates to systems and methods for portable assessment of labeled probes, and in particular labeled probes that are to be followed for extended periods of time.

2. Description of Background

Medical imaging techniques that rely on detection of emissions from tracers originating from within the body of the subject being imaged are widely used for diagnosis of various diseases. Nuclear physics-based molecular imaging techniques, such as positron emission tomography (PET) and single photon emission computed tomography (SPECT) allow functional imaging of subjects at the molecular level based on the use of radioactive isotopes. For example, SPECT is based on the use of radioisotopes that emit gamma rays and PET is based on the use of radioisotopes that emit positrons, which annihilate to produce gamma rays. In contrast to nuclear imaging techniques, fluorescence based optical imaging techniques do not involve ionizing radiation such as gamma rays. Instead, fluorescence imaging relies on the excitation of fluorophore tracers by a light source that results in the absorption of photons by the fluorophores, and the subsequent detection of photons emitted by the fluorophores as they decay from their excited state. A disadvantage of the various imaging techniques that rely on internal tracers, such as PET, SPECT and fluorescence imaging, is that they rely on the use of large scale and expensive scanners for the detection of emissions from the internal tracers, thereby requiring costly visits to radiology clinics.

SUMMARY OF THE INVENTION

Methods and devices disclosed herein provide a non-restrictive, portable photon-counting device which can be worn by a subject, e.g., on the head, arm, wrist and/or ankle, which can, in embodiments, allow tracking in the subjects body of a labeled probe over an extended period of time, e.g., over a period of days, or, e.g., for substantially longer than the time period for which a patient is typically monitored in a PET scan.

In on aspect, the invention features, an apparatus for detecting emissions from a labeled probe disposed within the body of a living subject. The apparatus comprises:

a detector configured to detect emissions from the labeled probe and to generate a signal based on the detected emissions, a transmitter configured to transmit the signal to a processor, and a biasing member configured to position the detector on the subject's body and allow the detector to be wearable by the living subject, wherein said apparatus is configured for detecting emissions and transmitting signals for at least X days, wherein X is 2.

In an embodiment, X is selected from 2, 3, 4, 5, 6, 7, 8, 9, 10, 15, 20, 30, 60, 90, or more days.

In an embodiment, said apparatus weighs less than 250, 500, 1,500, 2,000, 3,000 grams.

In an embodiment, said apparatus is configured such that the subject is able to walk while wearing the apparatus.

In an embodiment, said apparatus is configured such that the subject has his or her full range of motion with one or both arms while wearing the apparatus.

In an embodiment, said apparatus is configured such that the detector does not move relative to the region of the subject's body from which it detects emissions when the subject walks.

In an embodiment, all elements of the apparatus are disposed outside the subject's body.

In an embodiment, no element of the apparatus is transdermal or implanted in the subject's body.

In an embodiment, said apparatus is configured to allow detection of emissions from a preselected region of said subject.

In an embodiment, the apparatus comprises a plurality of detectors.

In an embodiment, each of the detectors of the plurality of detectors is configured to detect emissions from a preselected region of the subject.

In an embodiment, the apparatus comprises a first detector configured to allow detection of emissions from a first preselected region of said subject and a second detector first detector configured to allow detection of emissions from a second preselected region of said subject.

In an embodiment, said first and second regions overlap.

In an embodiment, said first and second regions do not overlap.

In an embodiment, said first and second regions are coextensive.

In an embodiment, said apparatus comprises N detectors, wherein N is equal to at least 1, 2, 3, 4, 5, 6, 7, 8, 9, 10, 20, or 30.

In an embodiment, each detector is configured to allow detection of emissions from a preselected region.

In an embodiment, at least 2, 3, 4, 5, 6, 7, 8, 9, or 10 of said preselected regions overlaps with one or more other preselected region.

In an embodiment, at least 2, 3, 4, 5, 6, 7, 8, 9, or 10 of said preselected regions does not overlap with another preselected region.

In an embodiment, a plurality of preselected regions are configured such that detection of emissions from them allows determination the levels, e.g., the levels over time, of the labeled probe.

In an embodiment, one or a plurality of detectors are configures such that emissions from the brain, and optionally a region away from the brain, e.g., the arm or leg can be detected.

In an embodiment, a plurality of detectors is arranged such that the plurality of signals form an image indicative of a location of the labeled probe within the living subject.

In an embodiment, the plurality of detectors is arranged in a ring configuration.

In an embodiment, the apparatus comprises a first detector having a preselected region that includes a target region or structure and a second first detector having a preselected region that does not includes the target region or structure.

In an embodiment, the detector is configured to detect emissions in at least one of a gamma ray and an infrared spectral range.

In an embodiment, the detector comprises a charge coupled device having a scintillation crystal, e.g., a removable scintillation crystal.

In an embodiment, the detector comprises one of a Geiger counter, an avalanche photodiode and a charge coupled device.

In an embodiment, said apparatus comprises a self-contained power source.

In an embodiment, the power source provides power for the detector and the transmitter.

In an embodiment, a detector is disposed on a first biasing member and the power source is disposed on a second biasing member.

In an embodiment, the transmitter is configured to transmit the signal wirelessly and the processor is located at a remote site.

In an embodiment, the transmitter is configured to receive signals from a plurality of detectors.

In an embodiment, the apparatus comprises a plurality of transmitters including the transmitter, each transmitter of the plurality of transmitters corresponding to at least one detector of the plurality of detectors and being configured to transmit at least one signal of the plurality of signals to the processor.

In an embodiment, said biasing member disposes a detector on the body of the subject.

In an embodiment, the biasing member surrounds a portion of the subject's body.

In an embodiment, the biasing member is configured to have a circumference, and the circumference is adjustable.

In an embodiment, the biasing member is formed from flexible material and is configured to be disposed around a portion of the subject's body.

In an embodiment, the portion of the subject's body is selected from the head, neck, arm, wrist, leg, ankle, abdomen, chest, or stomach.

In an embodiment, the biasing member comprises a band.

In an embodiment, the band is formed of stretchable material.

In an embodiment, the biasing member comprises one of a head-band, an arm-band, a wrist-band, an ankle-band and a waist-band.

In an embodiment, the apparatus further comprises a plurality of biasing members, each biasing member of the plurality of biasing members disposes at least one detector of the plurality of detectors and each biasing member further being configured to be wearable proximate to a different portion of the living subject.

In an embodiment, the apparatus further comprises a first biasing member for disposing a detector on the subject's body and a second biasing member for disposing a transmitter on the subject's body.

In an embodiment, the biasing member is configured to be wearable in proximity to a target portion of the living subject and the detector is configured to generate the signal indicative of the of the labeled probe within the target portion, the labeled probe being targeted to the target portion of the living subject.

In an embodiment, a plurality of detectors are configured with a biasing member such that the plurality of signals indicative of the pharmacokinetic property form an image indicative of a location distribution of the labeled probe within the living subject.

In an embodiment, a plurality of detectors is configured with a biasing member such that the plurality of signals are indicative of the concentration of the labeled probe in a preselected region or structure.

In an embodiment, said signal is indicative of the health or disease status of the subject.

In an embodiment, said signal is indicative of a target compound or structure bound by the labeled probe.

In an embodiment, said signal is indicative of the presence or level of a disorder, or disease state.

In an embodiment, said disorder, or disease state is selected from a neoplastic disorder, e.g., cancer, inflammation, a neurological disorder, e.g., a neurodegenerative disorder, e.g., Alzheimer's Disease.

In an embodiment, said signal is indicative of the presence of the labeled probe in a preselected region of said subject.

In an embodiment, the signal is indicative of the concentration of the labeled probe as a function of time.

In an embodiment, said signal is indicative of a pharmacokinetic property of the labeled probe or precursor thereof.

In an embodiment, said signal is indicative of a pharmacodynamic property of the labeled probe or precursor thereof.

In an embodiment, said signal is indicative of one or more of absorption, distribution, metabolism, and excretion of the labeled probe.

In an embodiment, said signal is indicative of the time course of one or more of absorption, distribution, metabolism, and excretion of the labeled probe.

In an embodiment, said labeled probe is a product of a reaction involving a precursor labeled probe administered to said subject.

In an embodiment, said signal is indicative of the concentration of the labeled probe at a site.

In an embodiment, said signal is indicative of the concentration of the labeled probe at a site and an effect of the labeled probe.

In an embodiment, said labeled probe is configured such that, e.g., with a single administration, it produces emissions detectable by the detector for at least X days, wherein X is 1 or greater.

In an embodiment, X is selected from 2, 3, 4, 5, 6, 7, 8, 9, 10, 15, 20, 30, 60, 90, or more days.

In an embodiment, said labeled probe is configured such that, upon 1, 2, 3, 4, 5, 6, 7, 8, 9, 10, 11, 12, 13, or 14 administrations, it produces emissions detectable by the detector for at least X days, wherein X is 1 or greater.

In an embodiment, X is selected from 2, 3, 4, 5, 6, 7, 8, 9, 10, 15, 20, 30, 60, 90, or more days.

In an embodiment, said labeled probe is has affinity for a compound or structure in the subject's body.

In an embodiment, said labeled probe comprises and antibody molecule, a ligand molecule, receptor a receptor molecule, or small molecule having affinity for a target.

In an embodiment, said labeled probe is a substance administered to said subject.

In an embodiment, said labeled probe comprises a product of a reaction involving a precursor labeled probe administered to said subject.

In an embodiment, said labeled probe comprises a product arising from metabolism of a precursor labeled probe administered to said subject.

In an embodiment, said labeled probe comprises a moiety that emits a gamma, a positron, or a photon.

In an embodiment, said labeled probe comprises a moiety that emits in the infrared range.

In an embodiment, the moiety comprises one of a radionuclide and a fluorophore.

In an embodiment, the moiety is covalently bonded to an atom of the probe.

In an embodiment, the labeled probe emits emissions in at least one of a gamma ray and an infrared spectral range.

In an embodiment, the labeled probe comprises a therapeutic agent.

In an embodiment, the labeled probe comprises a metabolized therapeutic agent.

In an embodiment, the labeled probe comprises a diagnostic agent.

In an embodiment, the labeled probe comprises a metabolized diagnostic agent.

In an embodiment, the apparatus further comprises:

a plurality of detectors, the plurality of detectors being configured to detect emissions from the labeled probe and to generate a plurality of signals, each detector of the plurality of detectors being configured to generate a respective signal of the plurality of signals based on emissions detected by that detector.

In an embodiment, the plurality of signals form an image indicative of a concentration of the labeled probe within the living subject.

In an embodiment, a plurality of detectors are arranged within a biasing member such that the plurality of signals indicative of the pharmacokinetic property form an image indicative of a location distribution of the labeled probe within the living subject.

In an embodiment, said preselected region comprises a region of the brain.

In an embodiment, the apparatus comprises a plurality of detectors configured to collect emissions from the brain.

In an embodiment, a plurality of detectors configured and preselected regions configured such that at least 1, 10, 20, 30, 40, 50, 60, 70, 80, 90, or 99% of the brain falls within said regions.

In an embodiment, a plurality of detectors are arranged within a biasing member such that the plurality of signals indicative of the pharmacokinetic property form an image indicative of a location distribution of the labeled probe within the living subject.

In an embodiment, the plurality of detectors is arranged in a ring configuration.

In an embodiment, the biasing member disposes a plurality of detectors around the circumference of the head, the biasing member being configured to be wearable around the head of the living subject for measuring emissions from the labeled probe within the brain of the living subject.

In an embodiment, at least 2, 3, 4, 5, 6, 7, or 8 detectors are disposed around the circumference of the head.

In an embodiment, a plurality of detectors is configured with a biasing member such that plurality of detectors is arranged around the circumference of a portion of the body.

In an embodiment, the portion of the body is the neck, chest, stomach, arm, leg, wrist, or ankle.

In another aspect, the invention features, a method for assessment of a labeled probe disposed within the body of a subject, the method comprising:

providing or acquiring an apparatus for the detection of a labeled probe wherein the apparatus comprises:

a detector configured to detect emissions from a labeled probe and to generate a signal based on the detected emissions, optionally, a transmitter configured to transmit the signal to a processor, and a biasing member configured to allow the detector to be wearable by the living subject; and placing the detector on the subjects body such that emissions from the labeled probe can be detected, wherein said apparatus is configured to detect emissions and transmit signals for at least X days, wherein X is 1 or greater.

In an embodiment, X is selected from 2, 3, 4, 5, 6, 7, 8, 9, 10, 15, 20, 30, 60, 90, or more days.

In an embodiment, the labeling moiety, frequency of administration of the labeled probe, half-live of the labeling moiety, and half-life, e.g., serum half life, of the probe, are selected so as to allow for emission, detection and analysis over a sustained period of time.

In an embodiment, the labeling moiety, half-live of the labeling moiety, and half-life, e.g., serum half life, of the probe, are selected so as to allow for emission, detection and analysis over a sustained period of time, upon a single administration of the labeled probe, e.g., for at least X days where X is 1.

In an embodiment, X is selected from 2, 3, 4, 5, 6, 7, 8, 9, 10, 15, 20, 30, 60, 90, or more days.

In an embodiment, the method further comprises:

receiving the signal indicative of the detection of emissions from the labeled probe.

In an embodiment, emissions are detected for at least X days, wherein X is 1 or greater.

In an embodiment, X is selected from 2, 3, 4, 5, 6, 7, 8, 9, 10, 15, 20, 30, 60, 90, or more days.

In an embodiment, said signal is generated, transmitted, or received, for at least X days, wherein X is 1 or greater.

In an embodiment, X is selected from 2, 3, 4, 5, 6, 7, 8, 9, 10, 15, 20, 30, 60, 90, or more days.

In an embodiment, the detector is placed on the subject's body by the subject.

In an embodiment, the detector is place on the subject's body by a person other than the subject.

In an embodiment, the method comprises adjusting the biasing member to fit the subject's body.

In an embodiment, the method comprises adjusting the biasing member to fit the subject's head, arm, wrist, chest, stomach, leg, or ankle.

In an embodiment, the method comprises adjusting the circumference of the biasing member to fit the apparatus to the subject's body.

In an embodiment, the method comprises adjusting the circumference of the biasing member to fit the apparatus to the subject's head, arm, wrist, chest, stomach, leg, or ankle.

In an embodiment, the method comprises administering the labeled probe or a precursor of the labeled probe to the subject.

In an embodiment, the method comprises:

generating, transmitting, or receiving a first signal indicative of the detection of emissions from the labeled probe; and generating, transmitting, or receiving a second, or subsequent, signal indicative of the detection of emissions from the labeled probe.

In an embodiment, at least 0.5, 1, 2, 3, 4, 5, 6, 7, 8, 9, 10, 11, 12, 24, 48, 72, or 96 hours elapses between generating, transmitting, or receiving a first signal and generating, transmitting, or receiving the second signal or subsequent signal.

In an embodiment, at least X days, wherein X is 1 or greater, elapses between generating, transmitting, or receiving the first signal and generating or receiving the second signal or subsequent.

In an embodiment, X is selected from 2, 3, 4, 5, 6, 7, 8, 9, 10, 15, 20, 30, 60, 90, or more days.

In an embodiment, the apparatus is not removed from the subject's body between generating, transmitting, or receiving the first signal and generating or receiving the second signal or subsequent signal.

In an embodiment, the apparatus is removed from the subject's body between generating, transmitting, or receiving the first signal and generating, transmitting, or receiving the second signal or subsequent signal.

In an embodiment, the method further comprises:
generating, transmitting, or receiving a first signal indicative of the detection of emissions from the labeled probe during a first time period; and
generating, transmitting, or receiving a second signal indicative of the detection of emissions from the labeled probe during a second, or subsequent, time period.

In an embodiment, at least 0.5, 1, 2, 3, 4, 5, 6, 7, 8, 9, 10, 11, 12, 24, 48, 72, or 96 hours elapses between the end of the first time period and the beginning of the second, or subsequent, time period.

In an embodiment, at least X days, wherein X is 1 or greater, elapses between the end of the first time period and the beginning of the second, or subsequent, time period.

In an embodiment, X is selected from 2, 3, 4, 5, 6, 7, 8, 9, 10, 15, 20, 30, 60, 90, or more days.

In an embodiment, the method comprises generating, transmitting, or receiving a signal indicative of the detection of emissions from the labeled probe in the time period between the first and second, or subsequent, time periods.

In an embodiment, the apparatus is not removed from the subject's body between the first time period the second, or subsequent, time period.

In an embodiment, the apparatus is removed from the subject's body between the first time period the second, or subsequent, time period.

In an embodiment, the method further comprises:
generating, transmitting, or receiving signals indicative of the detection of emissions from the labeled probe during at least 2, 3, 4, 5, 6, 7, 8, 9, 10, 20, 30, 40, 50, or 60 time periods.

In an embodiment, said time periods are separated by at least 1, 10, 30, or 60 minutes.

In an embodiment, the method further comprises generating an assessment of the labeled probe.

In an embodiment, the signal is indicative of the presence of the labeled probe in a preselected region of said subject.

In an embodiment, the signal is indicative of the concentration of the labeled probe as a function of time.

In an embodiment, said signal is indicative of a pharmacokinetic property of the labeled probe.

In an embodiment, said signal is indicative of a pharmacodynamic property of the labeled probe.

In an embodiment, the signal is indicative of one or more of absorption, distribution, metabolism, and excretion of the labeled probe.

In an embodiment, said signal is indicative of the time course of one or more of absorption, distribution, metabolism, and excretion of the labeled probe.

In an embodiment, said labeled probe is a product of a reaction involving a precursor labeled probe administered to said subject.

In an embodiment, said signal is indicative of the concentration of the labeled probe at a site.

In an embodiment, said signal is indicative of the concentration of the labeled probe at a site and an effect of the labeled probe.

In an embodiment, said signal is indicative of the health or disease status of the subject.

In an embodiment, said signal is indicative of the presence, incidence, stage, progress, or level of a disorder, or disease state.

In an embodiment, said signal is indicative of response to a treatment.

In an embodiment, said disorder, or disease state is selected from a neoplastic disorder, e.g., cancer, inflammation, a neurological disorder, e.g., a neurodegenerative disorder, e.g., Alzheimer's Disease.

In an embodiment, the method further comprises:
receiving the signal indicative of the detection of emissions from the labeled probe; and
generating a health status of the living subject based on the signal.

In an embodiment the method further comprises:
providing a plurality of bands for wearing proximate a plurality of target portions of the living subject, each band to be worn proximate a respective target portion of the plurality of target portions, each band including at least one detector for detecting emissions from the labeled probe and for generating at least one signal indicative of the detection of emissions.

In an embodiment, the method further comprises:
receiving a plurality of signals from the plurality of bands, the plurality of signals including the at least one signal from each band of the plurality of bands; and
generating an assessment of the pharmacokinetics of the probe within the plurality of target portions based on the plurality of signals.

In an embodiment, generating the assessment further includes generating at least one of a location distribution and a concentration distribution of the probe based on the plurality of signals.

In an embodiment, the method further comprises:
labeling the probe or precursor probe with a label.

In another aspect, the invention features, a method for assessment of a labeled probe disposed within the body of a subject, the method comprising:
receiving, from a wearable apparatus comprising a photon detector, a signal based on the detection of emissions from the labeled probe disposed within the body of the subject;
generating an assessment of the labeled probe based on the signal,
thereby assessing a labeled probe.

In an embodiment, the signal is transmitted wirelessly.

In an embodiment, the apparatus comprises:
a detector configured to detect emissions from the labeled probe and to generate a signal based on the detected emissions,
optionally, a transmitter configured to transmit the signal to a processor, and
a biasing member configured to allow the detector to be wearable by the living subject.

In an embodiment, the assessment is generated with a processor configured to receive the signal and to generate an assessment of the labeled probe based on the signal.

In another aspect, the invention features, a method for assessment of a labeled probe, the method comprising:
detecting emissions from the labeled probe, administered, e.g., injected, into a living subject using a detector worn by the living subject;
generating a signal based on the detecting, the signal being indicative of a pharmacokinetic property of the labeled probe; and transmitting the signal to a processor for assessing the pharmacokinetic property of the labeled probe.

In an embodiment, the method further comprises:
administering the labeled probe or a precursor of the labeled probe into the living subject.

In an embodiment the method further comprises:
receiving the signal by the processor located at a remote site; and
processing the signal to assess the pharmacokinetic property of the labeled probe.

In an embodiment, the labeling moiety, frequency of administration of the labeled probe, half-live of the labeling moiety, and half-life, e.g., serum half life, of the probe, are selected so as to allow for emission, detection and analysis over a sustained period of time.

In an embodiment, the labeling moiety, half-live of the labeling moiety, and half-life, e.g., serum half life, of the probe, are selected so as to allow for emission, detection and analysis over a sustained period of time, upon a single administration of the labeled probe, e.g., for at least X days where X is 1.

In an embodiment, X is selected from 2, 3, 4, 5, 6, 7, 8, 9, 10, 15, 20, 30, 60, 90, or more days.

In an embodiment, the method further comprises: receiving the signal indicative of the detection of emissions from the labeled probe.

In an embodiment, emissions are detected for at least X days, wherein X is 1 or greater.

In an embodiment, X is selected from 2, 3, 4, 5, 6, 7, 8, 9, 10, 15, 20, 30, 60, 90, or more days.

In an embodiment, said signal is generated, transmitted, or received, for at least X days, wherein X is 1 or greater.

In an embodiment, X is selected from 2, 3, 4, 5, 6, 7, 8, 9, 10, 15, 20, 30, 60, 90, or more days.

In another aspect, the invention features, a system for assessment of a labeled probe in living subject, the system comprising:
a detector configured to detect emissions from the labeled probe and to generate a signal based on the detected emissions,
a transmitter configured to transmit the signal to a processor,
a biasing member configured to allow the detector to be wearable by the living subject; and
a processor configured to receive the signal and to generate an assessment of the labeled probe based on the signal.

In an embodiment, the labeling moiety, frequency of administration of the labeled probe, half-live of the labeling moiety, and half-life, e.g., serum half life, of the probe, are selected so as to allow for emission, detection and analysis over a sustained period of time.

In an embodiment, the labeling moiety, half-live of the labeling moiety, and half-life, e.g., serum half life, of the probe, are selected so as to allow for emission, detection and analysis over a sustained period of time, upon a single administration of the labeled probe, e.g., for at least X days where X is 1.

In an embodiment, X is selected from 2, 3, 4, 5, 6, 7, 8, 9, 10, 15, 20, 30, 60, 90 or more days.

In an embodiment, the method further comprises:
receiving the signal indicative of the detection of emissions from the labeled probe.

In an embodiment, emissions are detected for at least X days, wherein X is 1 or greater.

In an embodiment, X is selected from 2, 3, 4, 5, 6, 7, 8, 9, 10, 15, 20, 30, 60, 90, or more days.

In an embodiment, said signal is generated, transmitted, or received, for at least X days, wherein X is 1 or greater.

In an embodiment, X is selected from 2, 3, 4, 5, 6, 7, 8, 9, 10, 15, 20, 30, 60, 90, or more days.

A kit comprising:
a) an apparatus for detecting emissions from a labeled probe disposed within the body of a living subject, the apparatus comprising one or more or all of:
a detector configured to detect emissions from the labeled probe and to generate a signal based on the detected emissions,
a transmitter configured to transmit the signal to a processor, and
a biasing member configured to position the detector on the subject's body and allow the detector to be wearable by the living subject, wherein said apparatus is configured for detecting emissions and transmitting signals for at least X days, wherein X is 1;
b) a labeled probe, or precursor thereof, suitable for allowing detection of emissions from the subject for at least X days, wherein X is 1, e.g., by one, two, or three administrations.

In an embodiment, X is selected, independently, from 2, 3, 4, 5, 6, 7, 8, 9, 10, 15, 20, 30, 60, 90, or more days.

The devices and methods described herein provide for remote assessment of subject health status, disease state, and drug pharmacokinetics.

Embodiments of the invention provide a non-restrictive, portable photon-counting device which can be worn by a subject, e.g., on the head, arm, wrist and/or ankle, which can, in embodiments, allow tracking in the subjects body of a labeled probe over an extended period of time, e.g., over days or weeks, e.g., substantially longer than the time period for which a patient is typically monitored in a PET scan. The device allows quantitative kinetic measurement of molecular compounds in a living subject. Compounds of interest can to be labeled with select radionuclides or fluorophores enabling the production of emissions across a broad spectrum of energies. These emissions are subsequently detected by the photon-counting device in any location and remotely reported back to researchers or clinicians via computer or mobile telecommunications devices. Typically, the probe and the labeled moiety are selected such that the combination of half-life in the serum (or other relevant compartment) and the half-life of the emitter together allow monitoring the labeled probe for days, weeks or even months.

Devices and methods of provided herein allow for minimally invasive methodologies to characterize the pharmacokinetic and pharmacodynamic behavior of diagnostic and therapeutic agents inside a living subject's body. Nuclear physics-based molecular imaging techniques, such as positron emission tomography (PET) or single photon emission computed tomography (SPECT), and fluorescence based optical imaging techniques offer such methodologies. PET and SPECT imaging are highly sensitive and have demonstrated great scientific and clinical value. In current practice however, both techniques require access to highly specialized clinic based scanners and radiologists thus adding significant expense. In the case of longer half-life isotope labeled compounds, repeated returns to the imaging facility are required for serial imaging scans of a subject. This poses logistical and economic constraints and thereby limits the full potential of PET and SPECT methodologies.

Fluorescence-based imaging techniques are widely used in preclinical research. Because they do not require use of a radioactive tracer, fluorescence methods are actively being pursued for clinical translation where they will face similar requirements and restrictions as PET and SPECT.

Devices and methods provided herein mitigate these restrictions by providing a portable photon-counting device that can minimize the need for costly hospital or imaging clinic based nuclear medicine/radiology studies, and can allow for improved exploitation of long half-life radioisotopes and/or fluorophores. Photon-monitoring devices enable low-cost, quantitative, non-invasive nuclear assays of drug and diagnostic agent kinetics within a subject over multiple biological half-lives. By allowing for portability and remote monitoring, devices and methods described herein can also bring the medical benefits of PET and SPECT technologies to parts of the world where scanners and radiologists are not readily available.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures.

DETAILED DESCRIPTION

Definitions

Figure 1A:
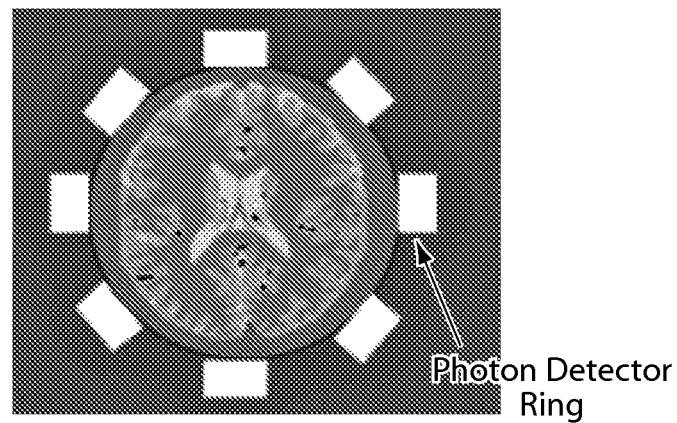
FIG. 1A is a top view of one embodiment of an apparatus having a plurality of detectors arranged in a ring configuration around a wearable band for brain imaging according to aspects of the present invention.

An antibody molecule, as used herein refers to an antibody or an antigen binding fragment thereof. Antibodies include IgA, IgG and IgE antibodies. They can be monospecific, polyspecific, non-human human, humanized, CDR-grafted or chimeric. Antibody molecules include single chain antibodies.

Labeled probe, as used herein, refers to a compound that produces a detectable emission. In embodiments the labeled probe has specific affinity for a target. E.g., the probe can be an antibody molecule, ligand molecule, receptor molecule, or small molecule having affinity for a target. Other examples of labeled probes include small molecule drugs and naturally occurring metabolites. Typically, the probe and the labeled moiety are selected such that the combination of half-life in the serum (or other relevant compartment) and the half-life of the emitter together allow monitoring the labeled probe for days, weeks or even months. In embodiments the labeled probe is configures such that it produces emissions detectable by the detector for at least X days, wherein X is 1 or greater. In embodiments, X is selected from 2, 3, 4, 5, 6, 7, 8, 9, 10, 15, 20, 30, 60, 90, or more, days.

A ligand molecule, as used herein refers to a ligand or a receptor binding fragment thereof.

Pharmacokinetics, as used herein, refers to time course of drug absorption, distribution, metabolism, and excretion. The effects of a drug, both desired and undesired, can be related to the presence or concentration of a drug at a site in the body, e.g., the site of action.

Pharmacodynamics, as used herein, refers to the relationship between the concentration of a drug at a site, e.g., the site of action and one or more effects of the drug.

Preselected region, as used herein in the context of a detector, is the region of the body from which emissions are detected by the detector.

A receptor molecule, as used herein refers to a receptor, or a ligand binding fragment thereof.

Wearable, as used herein, refers to a device that is of sufficiently compact size, of sufficiently low weight, and which is sufficiently well secured to the subject's body such that the subject can wear the device and still have substantially full range of motion, e.g., the subject is able to walk while wearing the device. In embodiments wearing the device does not substantially impact the ability of the subject to walk 100 meters. In embodiments wearing the device does not substantially impact the time it takes the subject to walk 100 meters. In embodiments wearing the device does not increase the subject's pulse rate by more than 20% as measured at the end of walking 100 meters, as compared with walking the same course without wearing the device. In embodiments, the device does not have a wired connection to the processor.

Labeled Probes

A labeled probe can be a drug, or other compound the presence or distribution of which can be followed. Labeled probes include, by way of example, drugs, drug metabolites, or molecules having an affinity with a target compound or structure. A precursor of the labeled probe can be administered to the subject, and in embodiments, the labeled probe arises from the precursor being metabolized or otherwise interacting with the subject's body.

In embodiments, a labeled probe can be an antibody molecule, a ligand molecule, a receptor molecule, or small molecule, having affinity for a target. Some labeled probes have high affinity for a target and localize by virtue of that affinity. Some labeled probes do not have high affinity for a target, but can, in embodiments, be localized in a target region.

Probes with affinity for components involved in a variety of disease states, structures, regions or organs, or stages of development, can be used in the methods disclosed herein. E.g., probes that are relevant to inflammation, unwanted cell proliferation, e.g., cancer, or neurologic structures, e.g., CNS or peripheral nervous structures or regions, or probes with affinity for components associated with neurological diseases or degeneration, e.g., Alzheimer's and Parkinson's disease, can be used with methods and devices described herein.

Exemplary probes, e.g., for the analysis of inflammation related processes, disorders or target regions, include molecules having a specific binding affinity, e.g., an antibody molecule for an integrin, ICAM1, VCAM1, laminin, vitronectin, or fibronectin.

Exemplary probes, e.g., for the analysis of cancer, include molecules having a specific binding affinity, e.g., an antibody molecule for PSMA, Estrogen receptor (ER)/progesterone receptor (PR), TGF-beta receptor 2 (TGF-β-R2), platelet-derived growth factor receptor (PDGFR), CXCR4 (CD184), CXCL12, stromal fibroblast activation protein (FAP). Urokinase receptor (uPAR; CD87), SMAD4) CD10 (a cell surface metalloprotease), CD10, hrombospondin-1

(TSP-1), CD208, CD3, CD8, CD25, CD45RO or CD95L (CD154), CD4, CD8, CD57, CD62L, CCR7, CD103, CD49d and CXCR3), HLA-DR, CD98, CD80, CD86 and CD134, CD45RA, CD27, CD28, CCR7 CD127, CD29, CD49d, CD49f, CD56, CD154 [CD29, LFA-1 (CD11a/CD18), LFA-3 (CD58), CD9, CD37, CD53, CD63, CD81, CD82, CD151, tetraspanin 8, CD29, α3 (CD49c), α4 (CD49d), α6 (CD49f) and β4 (CD104), matrix metalloproteinases (MMP), e.g., MT1-MMP (MMP14); members of the Ig superfamily, e.g., ICAM-1 (CD54) and VCAM-1 (CD106), CD26, CD44, EpCAM (CD326), E-cadherin (CD324), beta-catenin ((3-catenin) and ADAM10, growth factor receptors, e.g., epidermal growth factor receptor (EGFR), insulin growth factor receptor (IGFR), vascular endothelial growth factor receptors (VEGFr), human epidermal growth factor receptor 2 (CD340, HER-2/neu, ErbB2 receptor tyrosine-protein kinase ErbB4, or Hepatocyte growth factor receptor (Met).

Exemplary probes, e.g., for the analysis of neurologic structures, e.g., CNS or peripheral nervous structures or regions, or probes with affinity for components associated with neurological diseases or degeneration, include molecules having a specific binding affinity, e.g., an antibody molecule for Beta-Amyloid Peptide (N-terminus), Choline Acetyltransferase (ChAT), Doublecortin, Glutamate Receptor (Metabotropic) Type 1 (mGluR1), Glutamate Receptor (Metabotropic) Type 2 (mGluR2), Glutamate Receptor (Metabotropic) Type 3 (mGluR3), Glutamate Receptor (Metabotropic) Type 5 (mGluR5), Glutamic Acid Decarboxylase-67 (GAD 67), Growth-Associated Protein, 43 kDa (GAP-43), Microtubule-Associated Protein (MAP2), Netrin, Neu-N (Fox 3), NF-H (Neurofilament 200 kDa), NF-L (Neurofilament Protein, 68 kDa), NF-M (Neurofilament 160 kDa), Neuron-Specific Enolase (NSE), Prostatic Acid Phosphatase (PAP)—A Pain System Marker, Peripherin, Synaptotagmin-1, TAU, Tyrosine Hydroxylase (TYH), Beta-Tubulin 3 (TUJ), Glial Fibrillary Acidic Protein (GFAP), CNPase (cyclic nucleotide phosphodiesterase), Coronin 1a, Integrin alpha-M (CD11b, MAC-1, OX-42 Antigen), Myelin Basic Protein (MBP), Nestin, Proteolipid Protein (PLP), P-Zero Myelin Protein (Pz0), or Vimentin protein.

In embodiments probe targets, e.g., the antigen bound by an antibody molecule, are molecules that are not intracellular, e.g., in embodiments, the target is a transmembrane, extracellular or secreted protein, e.g., a component of an extracellular matrix.

A labeled probe or precursor thereof can be administered with one or more additional agents, e.g., a therapeutic agent. Such embodiments allow monitoring of the affect of the labeled probe or precursor on the agent and vice versa.

Labeling Moieties

Labeled probes are labeled with a labeling moiety. A labeling moiety can be, by way of example, a radionuclide, e.g., a gamma emitter, e.g., $^{123}$I, $^{111}$In, or $^{99}$Tc or a positron emitter, e.g., $^{11}$C or $^{18}$F. In embodiments where light can be delivered to the labeled probe, e.g., in dermal applications, or other applications reached by ambient light or which can be illuminated, e.g., endoscopically, the labeling moiety can emit in the near infrared or fluoresce. In preferred embodiments, the labeling moiety, frequency of administration of the labeled probe, half-live of the labeling moiety, and half-life, e.g., serum half life, of the probe, are selected so as to allow for emission, detection and analysis over a sustained period of time.

In some embodiments, a probe, e.g., a drug of interest, may be labeled with photon-emitting moieties. The emitters fall into one of two broad categories based on the energy of the emitted photon: optical or nuclear.

Optical Probes

The optical probes include a probe, e.g., a drug, labeled with a fluorophore (also known as a fluorochrome) of interest. Such a fluorophore is activated by a light source at the appropriate frequency at which time the compound fluoresces at a characteristic wavelength (most often in the near-infrared; 550-800 nm; ~1 eV). There are many commercially available fluorophores with safety data for injection into humans. These approaches result in no radiation dose to the subject, half-life of existence significantly longer than the biological half-life of the probe. These are best used to detect probe at a range of a few cm due to the absorption of light in tissue.

Nuclear Emitters

Nuclear emitters for this application include of either single-photon gamma emitters or positron emitters. There are many single-photon gamma emitters in the range of 50 to 300 keV (not often described in terms of wavelength; on the order of a pm in wavelength). Example of such isotopes include: $^{99m}$Tc, $^{111}$In, $^{67}$Ga, $^{201}$Tl, $^{123}$I, etc. There are hundreds of FDA approved radiopharmaceuticals employing these radioisotopes. Half life of decay a radioisotope can be matched with biological half-life of the drug of interest and frequency of administration. These emitters have no tissue-depth limitation on signal source but do provide a radiation dose to the subject.

In addition to collecting signal from single-photon gamma emitters, positron emitters can be employed as their positron emissions produce a pair of 511 keV photons following electron-positron annihilation. Examples of such positron emitters currently used in the clinical environment include: $^{18}$F, $^{11}$C, $^{124}$I, $^{89}$Zr, $^{68}$Ga, $^{64}$Cu, etc. These emitters allow one to gain spatial resolution about the location of positron-electron annihilation through the collection of gamma-ray coincidence events on the detector headband but provide a radiation dose and are more difficult to measure.

Detectors

Various embodiments of the devices and systems disclosed herein may include one or more detectors configured to detect emissions from the labeling moieties. Given the broad range of photon energies described in the labeling moieties useful in the methods, systems and devices described herein, there exists a broad range of photon detection technologies corresponding to the characteristic photon emission.

The most common commercial photon detection technologies are CCD (charged-couple device) and CMOS (complementary metal oxide semiconductor) systems. Both have strengths and weaknesses and the relevant selection criteria for selection of a detector may be a function of required bandwidth, noise and cost. Both CCD and CMOS detectors are routinely available for use in conjunction with the optical labeling moieties. Thus, in embodiments wherein the labeling moiety is a fluorophore, the detector may include a photon detector such as a CCD detector or a CMOS detector.

Imaging gamma emissions is a more challenging endeavor given the stopping power required to image higher energy gammas. Gamma ray detectors and associated methods of detecting gamma rays include: direct measurement of the ionizing radiation via interaction with a low-pressure gas in a Geiger-Mueller tube (often called a Geiger counter); a scintillation material coupled with a light amplification device such as a photomultiplier tube, an avalanche photodiode or an image intensifier, and a readout mechanism that estimates position and energy for the incident event on the scintillation material; direct conversion devices such as CdZnTe semiconductor detectors that consist of pixelated arrays that can measure and readout gamma interactions. Advances in detector technologies and electronics have enabled the creation of miniature gamma detectors that allow their use in the wearable systems disclosed herein. In some embodiments, scintillation materials coupled with a CCD or CMOS detector can integrate gamma emissions over a period of time and estimate the amount of labeled moiety in the subject. In some embodiments, a detector may include a CCD having a removable scintillation crystal which may be used for both fluorescence (near-infrared photon emitting) and nuclear (gamma-ray photon emitting) imaging.

Transmitters

Various embodiments of the systems disclosed herein may include one or more transmitters. A transmitter may be associated with one or more detectors. The transmitter may be configured to receive one or more signals from one or more detectors and to transmit received signals wirelessly to a processor, such as a processor included in a computer system as described further below. In some embodiments, a transmitter may be included within the detector. In other embodiments, the transmitter may be separate from the detector and the transmitter may be configured to transmit signals through a network. A transmitter may be configured to transmit the signal wirelessly. For example, the transmitter may be a Bluetooth transmitter. In other examples, the transmitter may be any other type of wireless transmitter. A wireless transmitter allows apparatuses disclosed herein to be wearable, without any of the obstructions conventionally associated with a wired system. Further examples of transmitters and data transmission protocols are described below in relation to various computer systems.

Examples of Systems and Methods

Aspects and embodiments disclosed herein are directed to providing systems and methods for portable assessment of labeled probes. For example, exemplary systems disclosed herein may be used for pharmacokinetic assessment during the drug discovery and development process, or may be used for purposes of monitoring, diagnosis or treatment of health conditions of subjects.

In one embodiment, a portable detection apparatus may be configured to allow detection of emissions from radio-isotope-labeled and fluorophore-labeled drug candidates. One or more detectors can be worn by individuals pre and post administration, e.g., post injection, of a fluorophore-labeled (near infrared photon emitting) or radiolabeled (gamma-ray photon emitting) pharmaceutical or diagnostic molecule, thereby allowing the measurement of the pharmacokinetics of said molecule within the subject. Such devices can track and report serial pharmacokinetics without need for further clinical visit on the part of the individual, as data can be transmitted wirelessly to a server and recorded in a database.

In some embodiments, the apparatus may be configured to provide a read-out of the concentration of the radio-labeled pharmaceutical as a function of time. While the images or tomograms produced by this method may lack the visual localization acuity of conventional clinical systems, they enable an assessment of the pharmacokinetics of the labeled probe at a much lower cost and greater ease of use.

According to an exemplary method disclosed herein, an individual could visit a pharmacy or dedicated outpatient clinic to have a labeled probe, such as a radio-labeled or fluorescent-labeled probe, administered intravenously or via other routes. The subject could then leave the pharmacy or clinic and may wear a portable apparatus configured according to aspects of the present disclosure, such as a photon-counting band, so as to capture and report back data on behavior of the injected molecule from any remote location.

In some embodiments, a portable detection apparatus may be configured to generate qualitative and quantitative data about the distribution of a radioactive labeled probe in the brain. Such a portable device and associated method of detecting the radio-labeled probe can be of wide use in tracking the onset, progression, and treatment response of diseases such as Alzheimer's and Parkinson's disease.

Referring now to the drawings, FIG. 1A shows one example of an apparatus having a plurality of detectors arranged in a ring configuration in a biasing member such as a head band. The head band is shown to be worn around the head of a subject for imaging the brain. The embodiment of FIG. 1A includes eight detectors. However, other embodiments may include any number of detectors. The apparatus of FIG. 1A is configured to allow detection of emissions from labeled probed targeted to the brain of the subject.

Figure 1B:
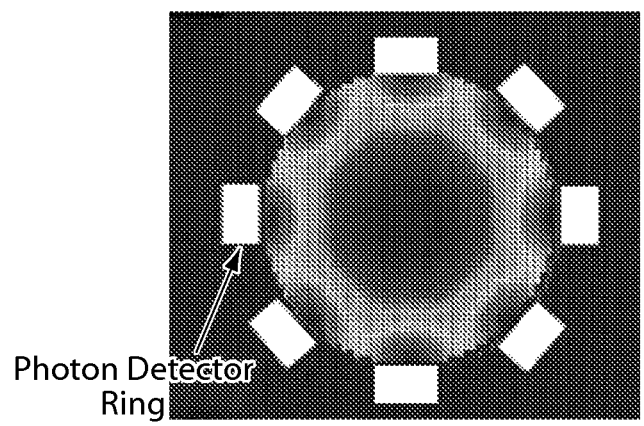
FIG. 1B is a sensitivity map showing a respective region of the brain corresponding to the field of view of each detector of the apparatus of FIG. 1A.
Figure 1C:
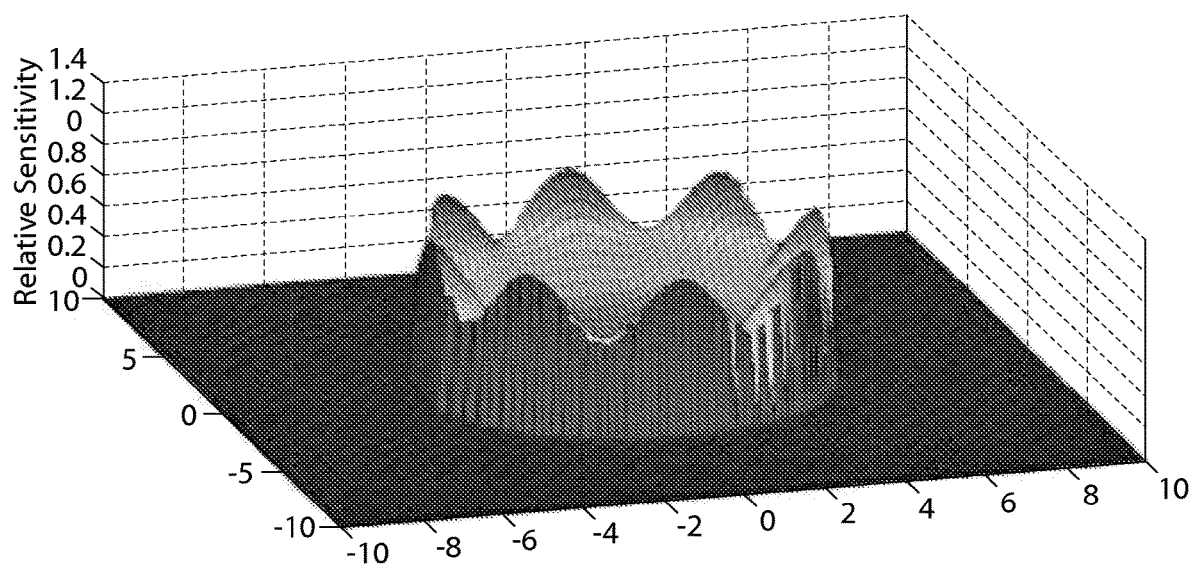
FIG. 1C is a perspective view of the sensitivity map of FIG. 1B.

FIG. 1B is a sensitivity map showing a respective region of the brain of the subject that corresponds to the field of view of each detector of the apparatus of FIG. 1A. FIG. 1C further shows a perspective view of the sensitivity map of FIG. 1B. Detector configurations and settings can be selected to provide an optimal sensitivity map for a given pharmacokinetic estimation task. In addition to providing pharmacokinetics for the entire brain, the apparatus of FIG. 1A could potentially provide information regarding the localization of the drug within the brain.

In some embodiments, the apparatus may include multiple biasing members, each including one or more detectors worn at different locations of the subject's body. For example, the head band may be supplemented with a detector elsewhere on the subject, e.g. the ankle, thereby allowing the estimation of the same pharmacokinetic parameters that are provided by clinical imaging systems.

The systems and methods disclosed herein include many advantages, including cost and convenience. Clinical imaging studies are expensive and have limited temporal windows for data acquisition. Systems and methods disclosed herein enable remote, inexpensive collection of comparable data based on portable photon-imaging detectors and secure, accessible network connections. By reducing the routine need for a dedicated PET, SPECT or optical scanner in a radiology clinic, there would be significant cost savings on the housing and maintenance costs of machines as well as on operator salaries for technicians and radiologists. Furthermore, by substituting a complicated in-hospital imaging procedure with an outpatient data solution, systems and methods disclosed herein can markedly improve the convenience of PET, SPECT, and optical imaging, thereby potentially increasing their use in medicine. Many remote communities in third world countries may not have access to hospitals with imaging scanners. Systems and methods disclosed herein can still bring the value of PET, SPECT and optical imaging to these communities without need for new infrastructure or travel. This convenience can therefore impact lives of patients in significant ways.

Various embodiments of the systems disclosed herein may include one or more detectors and may further include one or more transmitters. Furthermore, embodiments may include processors or computer systems or may be configured to communicate with remote processors and computer systems. Examples of various detectors, transmitters and computer systems that may be used in various embodiments are described in further detail below.

Computer Systems

Various aspects and functions described herein in accord with the present invention may be implemented as hardware, software, or a combination of hardware and software on one or more computer systems. Computer systems may be included in a portion wearable by a subject or may be external computer systems configured to receive data from the wearable detection apparatus and may be configured to process the data to generate various assessments, such as pharmacokinetic assessments and diagnostic assessments. The computer system may further be configured to process data by implementing various signal processing methods.

There are many examples of computer systems currently in use. Some examples include, among others, network appliances, personal computers, workstations, mainframes, networked clients, servers, media servers, application servers, database servers, web servers, and virtual servers. Other examples of computer systems may include mobile computing devices, such as cellular phones and personal digital assistants, and network equipment, such as load balancers, routers and switches. Additionally, aspects in accord with the present invention may be located on a single computer system or may be distributed among a plurality of computer systems connected to one or more communication networks.

For example, various aspects and functions may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Thus, the invention is not limited to executing on any particular system or group of systems. Further, aspects may be implemented in software, hardware or firmware, or any combination thereof. Thus, aspects in accord with the present invention may be implemented within methods, acts, systems, system placements and components using a variety of hardware and software configurations, and the invention is not limited to any particular distributed architecture, network, or communication protocol. Furthermore, aspects in accord with the present invention may be implemented as specially-programmed hardware and/or software.

Figure 2:
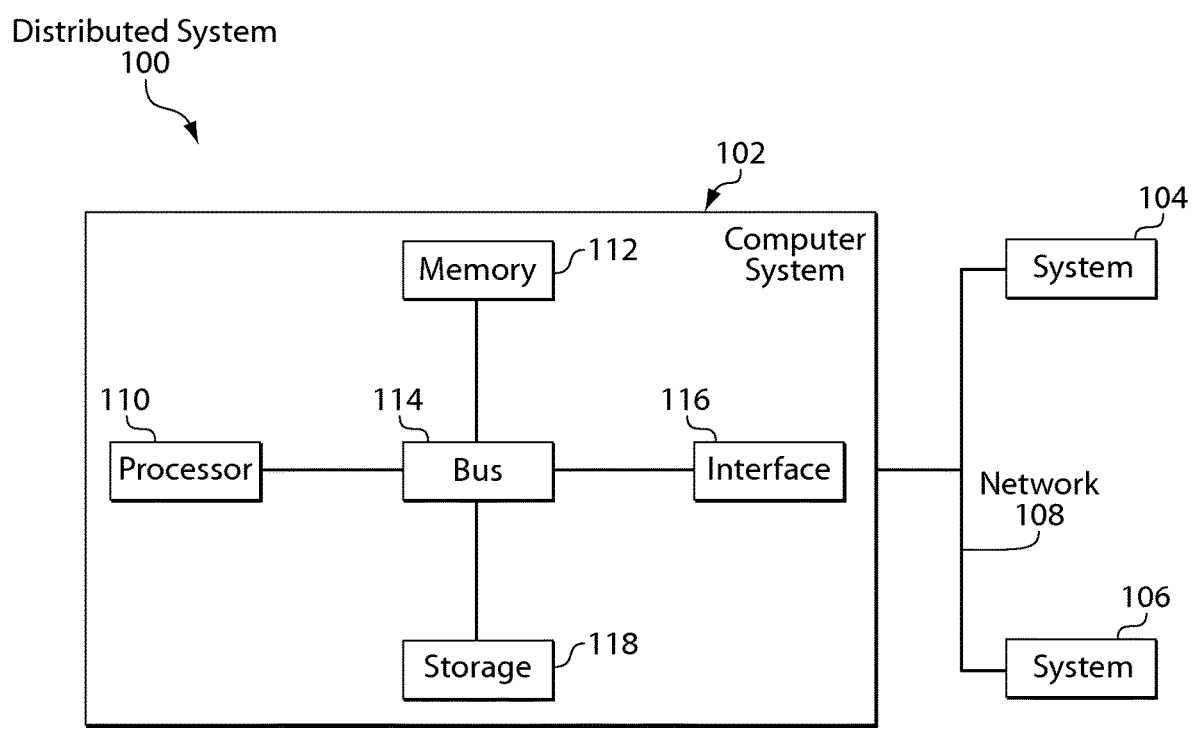
FIG. 2 is an exemplary computer system upon which various aspects of the present embodiments may be implemented.

FIG. 2 shows a block diagram of a distributed computer system 100, in which various aspects and functions in accord with the present invention may be practiced. The distributed computer system 100 may include one more computer systems. For example, as illustrated, the distributed computer system 100 includes three computer systems 102, 104 and 106. As shown, the computer systems 102, 104 and 106 are interconnected by, and may exchange data through, a communication network 108. The network 108 may include any communication network through which computer systems may exchange data. To exchange data via the network 108, the computer systems 102, 104 and 106 and the network 108 may use various methods, protocols and standards including, among others, token ring, Ethernet, Wireless Ethernet, Bluetooth, TCP/IP, UDP, HTTP, FTP, SNMP, SMS, MMS, SS7, JSON, XML, REST, SOAP, CORBA IIOP, RMI, DCOM and Web Services. To ensure data transfer is secure, the computer systems 102, 104 and 106 may transmit data via the network 108 using a variety of security measures including TSL, SSL or VPN, among other security techniques. While the distributed computer system 100 illustrates three networked computer systems, the distributed computer system 100 may include any number of computer systems, networked using any medium and communication protocol.

Various aspects and functions in accord with the present invention may be implemented as specialized hardware or software executing in one or more computer systems including the computer system 102 shown in FIG. 2. As depicted, the computer system 102 includes a processor 110, a memory 112, a bus 114, an interface 116 and a storage system 118. The processor 110, which may include one or more microprocessors or other types of controllers, can perform a series of instructions that manipulate data. The processor 110 may be a well-known, commercially available processor such as an Intel Pentium, Intel Atom, ARM Processor, Motorola PowerPC, SGI MIPS, Sun UltraSPARC, or Hewlett-Packard PA-RISC processor, or may be any other type of processor or controller as many other processors and controllers are available. The processor 110 may be a mobile device or smart phone processor, such as an ARM Cortex processor, a Qualcomm Snapdragon processor or an Apple processor. As shown, the processor 110 is connected to other system placements, including a memory 112, by the bus 114.

The memory 112 may be used for storing programs and data during operation of the computer system 102. Thus, the memory 112 may be a relatively high performance, volatile, random access memory such as a dynamic random access memory (DRAM) or static memory (SRAM). However, the memory 112 may include any device for storing data, such as a disk drive or other non-volatile storage device, such as flash memory or phase-change memory (PCM). Various embodiments in accord with the present invention can organize the memory 112 into particularized and, in some cases, unique structures to perform the aspects and functions disclosed herein.

Components of the computer system 102 may be coupled by an interconnection element such as the bus 114. The bus 114 may include one or more physical busses (for example, busses between components that are integrated within a same machine), and may include any communication coupling between system placements including specialized or standard computing bus technologies such as IDE, SCSI, PCI and InfiniBand. Thus, the bus 114 enables communications (for example, data and instructions) to be exchanged between system components of the computer system 102.

Computer system 102 also includes one or more interface devices 116 such as input devices, output devices and combination input/output devices. The interface devices 116 may receive input, provide output, or both. For example, output devices may render information for external presentation. Input devices may accept information from external sources. Examples of interface devices include, among others, keyboards, mouse devices, trackballs, microphones, touch screens, printing devices, display screens, speakers, network interface cards, etc. The interface devices 116 allow the computer system 102 to exchange information and communicate with external entities, such as users and other systems.

Storage system 118 may include a computer-readable and computer-writeable nonvolatile storage medium in which instructions are stored that define a program to be executed by the processor. The storage system 118 also may include information that is recorded, on or in, the medium, and this information may be processed by the program. More specifically, the information may be stored in one or more data structures specifically configured to conserve storage space or increase data exchange performance. The instructions may be persistently stored as encoded signals, and the instructions may cause a processor to perform any of the functions described herein. A medium that can be used with various embodiments may include, for example, optical disk, magnetic disk or flash memory, among others. In operation, the processor 110 or some other controller may cause data to be read from the nonvolatile recording medium into another memory, such as the memory 112, that allows for faster access to the information by the processor 110 than does the storage medium included in the storage system 118. The memory may be located in the storage system 118 or in the memory 112. The processor 110 may manipulate the data within the memory 112, and then copy the data to the medium associated with the storage system 118 after processing is completed. A variety of components may manage data movement between the medium and the memory 112, and the invention is not limited thereto.

Further, the invention is not limited to a particular memory system or storage system. Although the computer system 102 is shown by way of example as one type of computer system upon which various aspects and functions in accord with the present invention may be practiced, aspects of the invention are not limited to being implemented on the computer system, shown in FIG. 2. Various aspects and functions in accord with the present invention may be practiced on one or more computers having different architectures or components than that shown in FIG. 2. For instance, the computer system 102 may include specially-programmed, special-purpose hardware, such as for example, an application-specific integrated circuit (ASIC) tailored to perform a particular operation disclosed herein. Another embodiment may perform the same function using several general-purpose computing devices running MAC OS System X with Motorola PowerPC processors and several specialized computing devices running proprietary hardware and operating systems.

The computer system 102 may include an operating system that manages at least a portion of the hardware placements included in computer system 102. A processor or controller, such as processor 110, may execute an operating system which may be, among others, a Windows-based operating system (for example, Windows NT, Windows 2000/ME, Windows XP, Windows 7, or Windows Vista) available from the Microsoft Corporation, a MAC OS System X operating system available from Apple Computer, one of many Linux-based operating system distributions (for example, the Enterprise Linux operating system available from Red Hat Inc.), a Solaris operating system available from Sun Microsystems, or a UNIX operating systems available from various sources. The operating system may be a mobile device or smart phone operating system, such as Windows Mobile, Android or iOS. Many other operating systems may be used, and embodiments are not limited to any particular operating system.

The processor and operating system together define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, functions in accord with aspects of the present invention may be implemented using an object-oriented programming language, such as SmallTalk, JAVA, C++, Ada, or C# (C-Sharp). Other object-oriented programming languages may also be used. Alternatively, procedural, scripting, or logical programming languages may be used.

Additionally, various functions in accord with aspects of the present invention may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed placements, or any combination thereof. For example, a web page may be implemented using HTML while a data object called from within the web page may be written in C++. Thus, the invention is not limited to a specific programming language and any suitable programming language could also be used.

A computer system included within an embodiment may perform functions outside the scope of the invention. For instance, aspects of the system may be implemented using an existing product. Aspects of the system may be implemented on database management systems such as SQL Server available from Microsoft of Seattle, Wash.; Oracle Database from Oracle of Redwood Shores, Calif.; and MySQL from Sun Microsystems of Santa Clara, Calif.; or integration software such as WebSphere middleware from IBM of Armonk, N.Y. However, a computer system running, for example, SQL Server may be able to support both aspects in accord with the present invention and databases for sundry applications not within the scope of the invention.

Administration

A labeled probe or precursor thereof can be administered to a subject, e.g., a human subject, by a variety of methods. A labeled probe or precursor thereof, can be administered by one of the following routes: oral, intravenous, intramuscular, intra-arterial, subcutaneous, intraventricular, transdermal, interdermal, rectal, intravaginal, intraperitoneal, topical (as by liquids, powders, ointments, creams, sprays, or drops), mucosal, nasal, buccal, enteral, sublingual; intratracheal instillation, bronchial instillation, and/or inhalation; and/or as an oral spray, nasal spray, and/or aerosol.

The labeled probe or precursor can be administered once, or more than once. E.g., administration e can be repeated, e.g., once or twice or three times or more per week or during the time the subject is being monitored.

In embodiments, dosing can be adjusted according to a patient's rate of clearance. For example, a patient may be administered a second or follow-on dose if the level of labeled probe falls below a preselected reference.

In certain embodiments, the labeled probe or precursor thereof may be prepared with a carrier. In embodiments the carrier will protect the labeled probe or precursor thereof against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Controlled Drug Delivery (Drugs and the Pharmaceutical Sciences), Second Edition, J. Robinson and V. H. L. Lee, eds., Marcel Dekker, Inc., New York, 1987.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only, and the scope of the disclosure should be determined from proper construction of the appended claims, and their equivalents.

What is claimed is:

1. A mobile wearable apparatus comprising:
a first detector provided in unencumbered headwear wearable proximate to a head of a subject permitting the subject to be freely mobile, wherein the first detector detects emissions from a labeled probe within a brain of the subject and generates a first signal based on the detected emissions from the labeled probe within the brain of the subject;
a second detector provided in a biasing member wearable proximate to a second portion of the subject other than the head and permitting the subject to be freely mobile, wherein the second detector detects emissions from the labeled probe in the second portion and generates a second signal based on the detected emissions from the labeled probe in the second portion; and
a processor configured to generate an assessment of pharmacokinetics of the labeled probe within the brain and the second portion based on the first signal and the second signal, wherein the processor is configured to track movement of the labeled probe between the head and the second portion of the subject over time, wherein the second portion is at least one selected from the group of a neck, an abdomen, a chest, and a stomach.

2. The mobile wearable apparatus of claim 1, wherein the processor forms a tomographic image using the first signal and second signal.

3. The mobile wearable apparatus of claim 1, wherein the first detector and second detector detect a concentration of the labeled probe as a function of time.

4. The mobile wearable apparatus of claim 1, further comprising a power source.

5. The mobile wearable apparatus of claim 1, further comprising a headband, wherein the first detector is disposed on or within the headband.

6. The mobile wearable apparatus of claim 1, wherein the first detector and second detector detect if a concentration of the labeled probe falls below a preselected reference.

7. The mobile wearable apparatus of claim 1, wherein the first detector is a first plurality of detectors, and the first plurality of detectors generate a first plurality of signals in response to emissions detected from the labeled probe within the brain of the subject.

8. The mobile wearable apparatus of claim 7, wherein the first plurality of detectors are distributed such that the first plurality of signals are indicative of a concentration distribution of the labeled probe.

9. The mobile wearable apparatus of claim 8, wherein the first plurality of detectors are distributed such the first plurality of signals are indicative of the concentration distribution and a location distribution of the labeled probe.

10. The mobile wearable apparatus of claim 9, wherein the first plurality of signals are indicative of the location distribution of the labeled probe as a function of time and are indicative of the concentration distribution of the labeled probe as a function of time.

11. The mobile wearable apparatus of claim 9, wherein the first plurality of signals are indicative of the location distribution of the labeled probe as a function of time or are indicative of the concentration distribution of the labeled probe as a function of time.

12. The mobile wearable apparatus of claim 7, wherein the first plurality of detectors include at least two detectors that detect emissions from a first preselected region and a second preselected region.

13. The mobile wearable apparatus of claim 12, wherein said first and second preselected regions overlap.

14. The mobile wearable apparatus of claim 7, wherein the first plurality of detectors includes no more than 8 detectors.

15. The mobile wearable apparatus of claim 14, wherein the first plurality of detectors are arranged in a ring configuration around a circumference of the head.

16. The mobile wearable apparatus of claim 1, wherein the first detector detects emissions from a preselected region of the brain.

17. The mobile wearable apparatus of claim 1, wherein the first signal and second signal are indicative of a location distribution of the labeled probe.

18. The mobile wearable apparatus of claim 17, wherein the first signal and second signal are indicative of a concentration distribution of the labeled probe.

19. The mobile wearable apparatus of claim 18, wherein the first signal and second signal are indicative of a location distribution and the concentration distribution of the labeled probe as a function of time.

20. The mobile wearable apparatus of claim 1, wherein the first detector and second detector are configured to remain worn on the subject during generation of the first signal and generation of the second signal.

* * * * *